United States Patent [19]

Oita et al.

[11] Patent Number: 4,472,261
[45] Date of Patent: Sep. 18, 1984

[54] DISSOLVED OXYGEN GAS MEASURING ELECTRODE SYSTEM

[75] Inventors: Masahiro Oita, Kashiwara; Naohumi Tonoka, Katano, both of Japan

[73] Assignee: Matsushita Electric Industrial Co., Ltd., Kadoma, Japan

[21] Appl. No.: 482,556

[22] Filed: Apr. 6, 1983

[30] Foreign Application Priority Data

Apr. 9, 1982 [JP] Japan ................. 57-59994

[51] Int. Cl.³ .......................................... G01N 27/46
[52] U.S. Cl. ................................. 204/402; 204/415
[58] Field of Search ............................. 204/402, 415

[56] References Cited

U.S. PATENT DOCUMENTS

| | | | |
|---|---|---|---|
| 1,668,434 | 5/1928 | Todd | 204/402 |
| 3,070,539 | 12/1962 | Arthur et al. | 204/415 |
| 3,073,772 | 1/1963 | Wirz et al. | 204/402 |
| 3,155,603 | 11/1964 | Hart | 204/402 |
| 3,235,477 | 2/1966 | Keyser et al. | 204/415 |
| 3,402,116 | 9/1968 | Kaltenhauser et al. | 204/402 |
| 3,496,084 | 2/1970 | Stack | 204/415 |
| 3,563,875 | 2/1971 | Coulson | 204/405 |
| 3,574,079 | 4/1971 | Kalman | 204/405 |
| 3,718,567 | 2/1973 | Haddad et al. | 204/415 |
| 4,019,966 | 4/1977 | Remes et al. | 204/402 |

Primary Examiner—T. Tung
Attorney, Agent, or Firm—Wenderoth, Lind & Ponack

[57] ABSTRACT

An electrode system for measuring oxygen gas in a solution comprises a pair of electrodes consisting of an indicator electrode and a reference electrode immersed in an electrolyte solution and a membrane pressed against the indicator electrode. On the other side of the membrane, is a solution to be analyzed. In determination of gas in solution especially in blood, good reproducibility of data, a stable reading and a long performance life are obtained by rubbing the surface of the indicator electrode and rotating a magnetic stirrer on the membrane. These effective measures prevent the electrode and the membrane from being contaminated. Accordingly, continuous analysis of arterial blood can be achieved.

21 Claims, 5 Drawing Figures

FIG. 1
FIG. 2
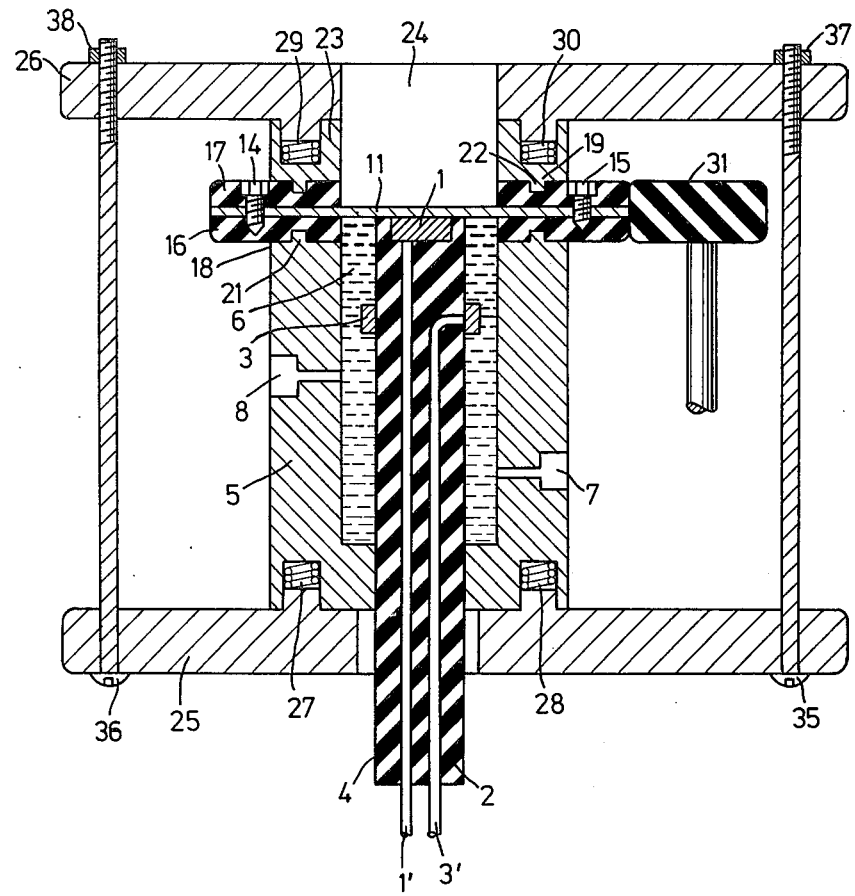
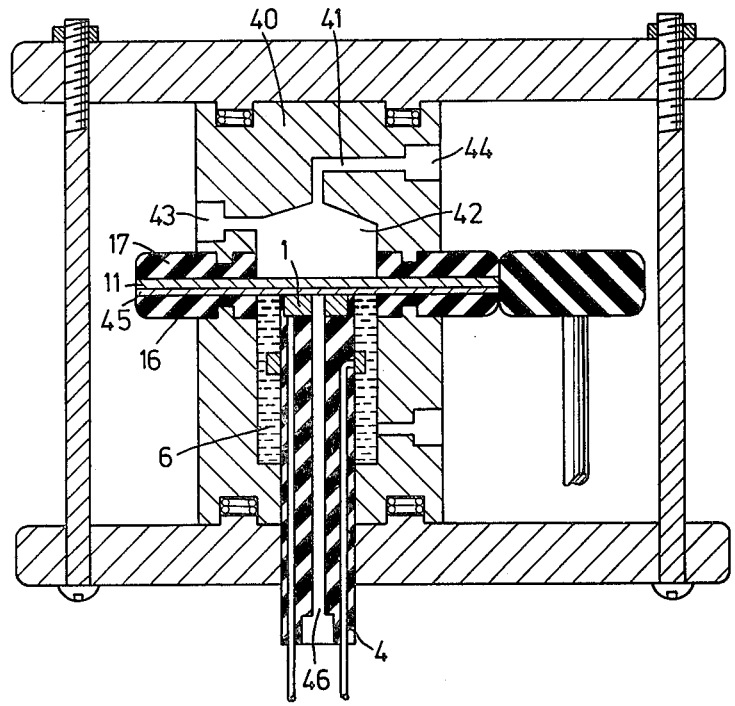

DISSOLVED OXYGEN GAS MEASURING ELECTRODE SYSTEM

BACKGROUND OF THE INVENTION

1. Field of the Invention

This invention relates to an electrode system for measuring oxygen gas concentration in a solution, especially in blood.

Determination of oxygen gas in blood has been conducted in clinical fields including diagnosis of various diseases of circulatory and respiratory organs, the examination of endocrine, metabolic, and digestive organ diseases, nacotism, and the control of respiratory function after operations. Much attention has been paid to oxygen concentration in blood of babies born immature and infants in a syncopic state. When oxygen is lacking in the blood it does not reach all parts of the body resulting in death or suffering from cerebral palsy. Conversely, if oxygen in the blood is in great excess it is responsible for diseases like retinitis (in immature babies).

Therefore, it is very important for a person treating a newly born baby or a seriously injured patient requiring artificial respiration to determine the content of oxygen or its partial pressure in blood, especially in arterial blood, in order to control their respiration.

2. Description of the Prior Art

There have been a few disclosures of electrodes and systems for the electrochemical analysis of oxygen in a solution such as blood.

U.S. Pat. No. 2,913,386 discloses an electrolytic device called a "CLARK ELECTRODE" for use in chemical analysis, and particularly a polarographic cell adaptable for use in making quantitative analysis, especially continuous analysis. It comprises an electrode pair supported in a predetermined spaced relationship and electrically connected by an electrolyte or a substance reactable to form an electrolyte, and a selectively permeable barrier for separating the electrode pair and the electrolyte or other substance from the composition to be analyzed.

U.S. Pat. No. 3,372,103 discloses an improved dissolved oxygen probe in order to obtain a fast response, a stable reading and a long performance life. In this probe, the surface of a lead anode is large relative to that of a platinum cathode, at least 30 to 1. The surface area of the lead rod in square inches relative to the volume of electrolyte in milliliters is greater than one.

U.S. Pat. No. 3,088,905 discloses an electrode system which is not affected by solution movement and other constituents in the test solution, for example proteins in blood or metal ions in industrial solutions. The negative electrode consisting of a platinum or gold wire is fixed co-axially within a silver tube acting as the positive electrode by means of an electrically insulating material such as glass, filling the space between the wire and tube. The whole thus forms a solid rod, one end of which is ground flat.

Briefly, an electrode system conventionally used for measuring oxygen content of a fluid comprises an indicator electrode and a reference electrode which are immersed in an electrolyte solution and an oxygen permeable membrane against which the indicator electrode is pressed. A sample solution to be analyzed is located on the other side of the membrane. Since a voltage of 0.4 volt to 0.8 volt is applied between the two electrodes, oxygen penetrating through the membrane is electrolized, resulting in a flowing polarographic current proportional to the concentration of oxygen in the sample solution.

In this type of electrode system, Ag/AgCl or Ag is used as a reference electrode. Concerning the Ag/AgCl electrode, its surface turns into an silver chloride rich electrode through electrolysis because of the dissolving of silver. On the other hand, silver deposits on the surface of the indicator electrode. When the amount of oxygen in some blood which is in contact with the membrane is determined, the coagulation of blood sometimes occurs on the surface of the membrane resulting in retardation of the response of a reading.

SUMMARY OF THE INVENTION

It is a primary object of the present invention to provide an oxygen gas measuring electrode system having a stable reading and good reproducibility of measurement value, and a fast response.

It is another object of the present invention to provide an effective electrode for measuring oxygen in blood which coagulates easily.

It is still another object of the present invention to provide an electrode system having a long performance life.

It is a further object of the present invention to provide an electrode system preferred for continuous analysis of a fluid such as blood.

It is a still further object of the present invention to provide an electrode system having means for automatically restoring the due function of the electrode and the membrane thereof.

The above and other objects and features of the present invention will appear hereinafter in detail, and only for purposes of illustration (but not limitation); specific embodiments of the invention are shown in the accompanying drawings.

BRIEF DESCRIPTION OF THE DRAWINGS

FIG. 1 is a cross-sectional view of an embodiment of an oxygen gas electrode system having a rotating membrane according to the present invention.

FIG. 2 is a cross-sectional view of an embodiment of a membrane-rotating electrode system for a flow-through analysis according to the present invention.

DESCRIPTION OF THE PREFERRED EMBODIMENTS

Figure 3:
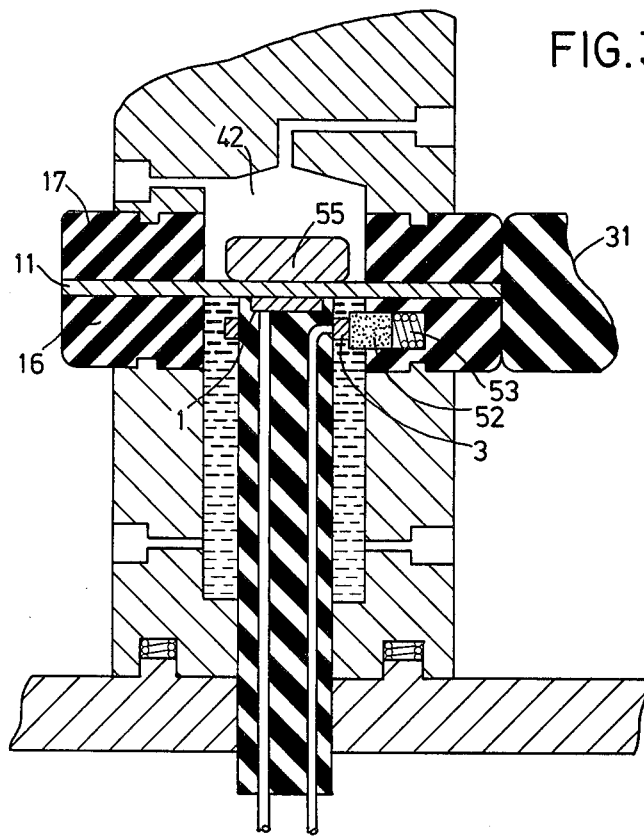
FIG. 3 is an enlarged fragmentary detail cross-sectional view of an embodiment of an electrode system according to the present invention.

A cross-sectional view of an oxygen gas measuring electrode system according to the present invention is shown in FIG. 1. An electrode shaft 4 is prepared in such a manner that an indicator electrode 1 of a precious metal such as gold and platinum is mounted on an end surface of shaft 4 covered by an insulating material 2 (made of such a material as plastic). An annular reference electrode 3 such as silver-silver chloride is mounted on the side surface of shaft 4 so as to surround shaft 4. Lead wires 1' and 3' running inside shaft 4 are connected with indicator electrode 1 and reference electrode 3, respectively so as to obtain electric signals from the electrodes. Electrode shaft 4 is attached to a bottom opening of an electrolytic cell 5 having an inlet 7 and an outlet 8 for an electrolyte solution 6 such as phosphite buffer solution. Accordingly, shaft 4 is immersed in solution 6.

Electrolysis of oxygen takes place between electrodes 1 and 3. The measurement of oxygen in a solution requires an oxygen permeable membrane 11, such as fluoride resin (i.e. Teflon), polycarbonate, polyethylene or polypropylene, which allows oxygen gas to pass through independently of the perviousness of any solution. Such a membrane, conventionally used, is so thin and easily damaged that reinforcement is necessary to make it easy to handle. However, according to the present invention, the periphery of membrane 11 is sandwiched between supporting materials consisting of two gear wheels 16 and 17, which are bound with screws 14 and 15. Otherwise, an adhesive may be applied between membrane 11 and gear wheels 16 and 17. Membrane 11, having the above mentioned reinforced periphery, is mounted on the top opening of the electrolytic cell 5 to cover indicator electrode 1, so that indicator electrode 1 is pressed lightly against membrane 11.

A circular projection 21 is formed on the top surface of electrolytic cell 5 so as to serve as a guide for rotation of gear wheels 16 and 17. Projection 21 is fitted to a circular groove 18 of gear wheel 16. Instead of providing projection 21, as a guide, it is also possible to form a groove on the top surface of cell 5 and insert an O-ring into two grooves facing each other.

In the same manner, gear wheel 17 also has a groove 19 in which is inlaid a projection 22 of a ring 23 which constitutes a test chamber 24. A gap between gear wheel 17 and ring 23 is mechanically sealed so as to prevent sample solution from leaking. The same is the case for a gap between gear wheel 16 and cell 5 so as to prevent the leaking of electrolytic solution 6.

All the construction elements are bound together between two plates 25 and 26 with screws 35 and 36 and nuts 37 and 38. Springs 27, 28, 29 and 30 are provided between plates 25 and 26 so as to adjust the tightening strength. Gear wheels 16 and 17 engage with another gear wheel 31 which is linked to a clutch (not shown) of a motor (not shown) and are rotated by the motor. Membrane 11 may overlap the surface of indicator electrode 1 so as to prevent silver from precipitating on the surface of indicator electrode 1 despite the occurrence of electrolysis. Accordingly, the surface of indicator electrode 1 is constantly kept clean during the measurement. In this electrode system, the sample solution to be analyzed is accessible from the top.

An electrolytic voltage ranging from 0.4 volts to 0.8 volts is applied between reference electrode 3 and indicator electrode 1 whereby oxygen gas that passes through membrane 11 is electrolized according to the following reaction:

$$O_2 + 2H_2O + 4e^- \rightarrow 4OH^- \tag{1}$$

As the result, the polarographic current is proportional to the oxygen content in the sample solution. Simultaneously, silvering takes place on the surface of indicator electrode 1.

A contrivance to eliminate the silver from the surface of the indicator electrode is an important point of the present invention. Briefly, the surface of the indicator electrode 1 is kept constantly clean by being rubbed with the membrane. As a result, the electrode system of the present invention gives a stable reading, has a long performance life, and shows good reproducibility of measurement values.

Another embodiment of the electrode system for flow-through measurement according to the present invention is shown in FIG. 2 as a modification of the electrode system illustrated in FIG. 1. A cap 40 having a channel 41 is mounted on gear wheel 17. A sample solution flows from an inlet 43 to an exit 44. A space defined by cap 40 and membrane 11 constitutes a sample chamber 42 for the flow-through measurement. Membrane 11 having thereunder a mesh 45, made of a material such as nylon or cotton, which directly contacts the surface of indicator electrode 1 is sandwiched between two gear wheels 16 and 17. This arrangement prevents the membrane 11 from wearing since the membrane 11 does not directly contact the electrode 1. This allows carrying out continuous analysis of dissolved oxygen for a long period of time without exchanging membrane 11.

An aperture 46 running through the inside of electrode shaft 4 serves as an inlet for electrolyte solution 6. Injecting electrolyte 6 from the aperture 46 can avoid the occurrence of air bubbles remaining on the surface of indicator electrode 1. During the analysis of oxygen such air bubbles render measurement values inaccurate and unstable. A main disadvantage of the deposition of silver on indicator electrode 1 has already been described.

Another disadvantage during the analysis is the gradual departure of the surface material of reference electrode 3 which conventionally consists of Ag/AgCl. This is due to gradual silver dissolution caused by the applied voltage, and gives rise to a gradual deviation of the measurement value with the lapse of time.

In addition, while the oxygen content of blood is continuously measured, blood coagulates and adheres to the membrane. This lowers the gas permeability of the membrane. Accordingly, the response rate of the electrode lowers and the reproducibility of the measurement becomes worse. Although this electrode system is mainly applied to the determination of oxygen concentration in blood, continuous analysis of the oxygen concentration in blood has been difficult because of the coagulation of blood.

Considering the above mentioned drawbacks, additional countermeasures according to the present invention are taken. The elimination of the coagulated blood can be carried out by placing a magnetic stirrer in the measuring chamber and rotating it on the membrane during continuous measurement. This system not only eliminates the coagulated blood from the membrane but also prevents further coagulation of blood on the membrane.

A fragmentary view of a modified embodiment of the electrode system considering the above measures is shown in FIG. 3. A magnetic stirrer 55 is placed in a test chamber 42 and rotated on membrane 11 by means of a magnet 50 attached to an axle 51 of a motor (not shown). A buffer consisting of a polishing rod 52 and a spring 53 for pushing rod 52 is attached to gear wheel 16. When gear 31 rotates, reference electrode 3, tightly contacting polishing rod 52, can be constantly polished so that the surface of electrode 3 is kept clean. In place of using the buffer, it is also possible to mount reference electrode 3 adjacent to indicator electrode 1 on the end surface of shaft 4 and to polish them at the same time by rotating membrane 11.

Figure 4:
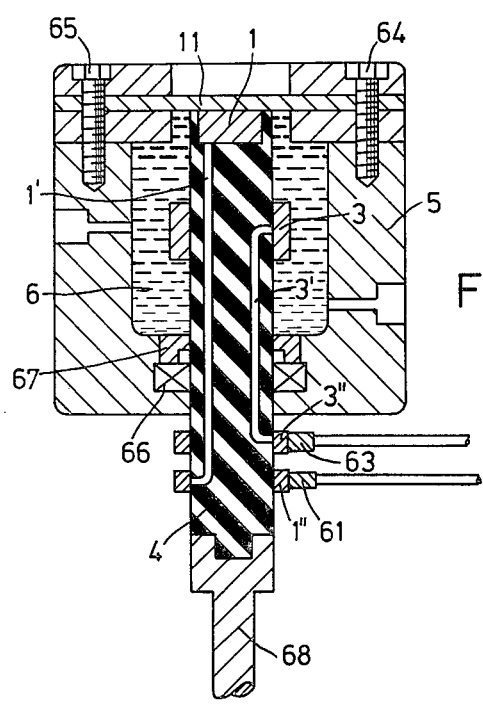
FIG. 4 is a cross-sectional view of an embodiment of an electrode shaft-rotating electrode system according to the present invention.

Next, an embodiment of an electrode shaft-rotating electrode system according to the present invention will be described. FIG. 4 illustrates a vertical cross section of a further embodiment of an electrode system according to the present invention, in which electrode shaft 4 is rotated and membrane 11 is fixed. As already shown in FIG. 1, on the end surface of electrode shaft 4, indicator electrode 1 is mounted. Also, ring shaped reference electrode 3 is mounted on the side surface of shaft 4. This shaft 4 is placed in electrolytic cell 5 which has top and bottom openings. A portion of shaft 4 sticks out through the bottom opening which is therein provided with a bearing 66 and an oil seal 67 for preventing electrolyte solution 6 from leaking through the opening during the rotation of shaft 4. Instead of using oil seal 67, a mechanical seal may be used. A conventional motor (not shown) is installed to rotate shaft 4 which is clutched at a motor axle 68.

Lead wire 1' links indicator electrode 1 to a circular electric contact 1" mounted around the side surface of shaft 4. Lead wire 3' links reference electrode 3 to another electric contact 3" mounted around the side surface of shaft 4. These contacts 1" and 3" are connected with brushes 61 and 63, respectively, from which electric signals based on the electrode reaction (1) can be finally obtained.

Membrane 11 with its periphery reinforced is fixed in the upper opening of cell 5 with screws 64 and 65 so as to lightly contact the surface of indicator electrode 1. Prior to fixing membrane 11, it is better to insert a gasket or an O-ring (not shown) between the periphery thereof for holding membrane 11 and the top surface of cell 5 so as to prevent electrolyte solution 6 from oozing out. The surface of indicator electrode 1 is constantly rubbed by membrane 11 while shaft 4 rotates. The instant silver is deposited on the surface of indicator electrode 1, it is immediately eliminated from the surface. Consequently, indicator electrode 1 is substantially maintained in its initial state without any contamination by deposited silver.

Figure 5:
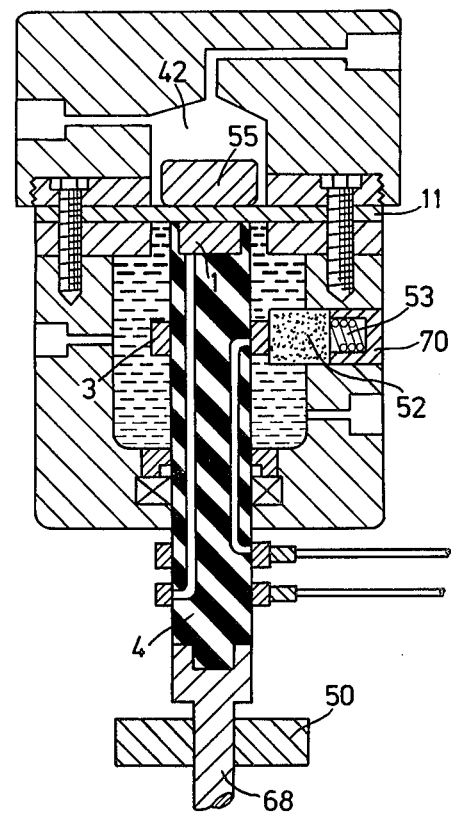
FIG. 5 is a cross-sectional view of an embodiment of an electrode shaft-rotating electrode system for continuous measurement according to the present invention.

Still another preferable embodiment of an electrode system according to the prevent invention is shown in FIG. 5. In this electrode system, not merely indicator electrode 1, but reference electrode 3 and membrane 11 as well, are constantly kept clean. As for reference electrode 3, its surface is polished by means of a buffer. The buffer which is attached in the side wall of electrolytic cell 5 comprises rod 52 of a polishing agent made of a material such as resin, SiC and buffing cloth, spring 53 for pushing rod 52 from behind and a container 70 for accommodating them. Spring 53 constantly presses polishing rod 52 so that reference electrode 3 comes in close contact with rod 52. Even in continuous measurement, this system helps reference electrode 3 maintain the same activity as it initially has.

As shown in FIG. 3, the same method of keeping the surface of membrane 11 clean may also be applied to this case. Magnetic stirrer 55 coated with resin for preventing it from rusting is placed in sample chamber 42. Stirrer 55 rotates and constantly rubs the surface of membrane 11 by means of magnet 50 attached to motor axle 68 which is linked to electrode shaft 4. Thus, even if a test solution is blood which is easily coagulates on membrane 11, its surface can be maintained as clean as it originally is.

The electrode system hereinbefore described is not restricted only to vertical use. But it can be used tilted, horizontally and upside down.

Various modifications and additions may be made to the above described electrode system without departing from the scope of the present invention. Accordingly, the invention disclosed herein shall be interpreted in an illustrative and not in a limiting sense.

What is claimed is:

1. An electrode system for measuring oxygen gas in a solution, comprising:
    a pair of electrodes including an indicator electrode and a reference electrode;
    an oxygen permeable membrane covering said indicator electrode so as to separate said pair of electrodes from said solution to be analyzed;
    a shaft mounting thereon said pair of electrodes;
    an electrolytic cell mounting therein said shaft and being filled with an electrolyte solution;
    means for pressing a surface of said membrane against a surface of said indicator electrode, the contacting surfaces of said membrane and said indicator electrode being parallel; and
    means for rotating at least one of said indicator electrode and said membrane in a direction parallel to said contacting surfaces so that the surface of said indicator electrode is rubbed with the surface of said membrane, thereby to be cleaned.

2. An electrode system according to claim 1, wherein said indicator electrode is mounted on an end surface of said shaft.

3. An electrode system according to claim 2, wherein said reference electrode is disposed adjacent to said indicator electrode on said end surface of said shaft.

4. An electrode system according to claim 1, wherein said means for pressing said membrane is a supporting member for reinforcing said membrane at the periphery thereof.

5. An electrode system according to claim 1, wherein said shaft is rotated and said membrane is fixed so as to cover an opening of said electrolytic cell.

6. An electrode system according to claim 1, wherein said membrane is rotated and said shaft is fixed in said electrolytic cell.

7. An electrode system according to claim 1, further comprising a body having a test chamber therein covering said membrane.

8. An electrode system according to claim 7, wherein said body has a channel therein for channeling therethrough into said chamber said solution to be analyzed.

9. An electrode system according to claim 7, further comprising in said test chamber a magnetic stirrer rotated by a magnet so as to rub the surface of said membrane opposite said indicator electrode.

10. An electrode system according to claim 9, wherein said magnetic stirrer is coated with resin.

11. An electrode system according to claim 1, further comprising a buffer pressed against said reference electrode so as to rub the surface of said reference electrode.

12. An electrode system according to claim 11, wherein said buffer comprises a polishing rod for rubbing the surface of said reference electrode, a spring for pushing said polishing rod toward said surface of said reference electrode and a receptacle for accommodating said polishing rod and said spring.

13. An electrode system according to claim 12, wherein said polishing rod is made of at least one of resin, SiC, $Al_2O_3$, and a buffing cloth.

14. An electrode system according to claim 1, wherein said membrane has a mesh underlaid so as to prevent said membrane from wearing out.

15. An electrode system according to claim 14, wherein said mesh is made of cotton or nylon.

16. An electrode system according to claim 1, wherein said shaft has an aperture running through the inside thereof for inputting said electrolyte solution.

17. An electrode system for measuring oxygen gas in a fluid, comprising:
a pair of electrodes including an indicator electrode and a reference electrode;
an oxygen permeable membrane;
a shaft mounting said indicator electrode on an end surface thereof and said reference electrode surrounding said shaft on the side surface thereof;
an electrolytic cell mounting therein said shaft and filled with an electrolyte solution, said shaft being immersed in said electrolyte solution;
means for reinforcing said membrane at the periphery thereof so that a surface of said membrane is in contact with a surface of said indicator electrode;
a buffer attached to a side wall of said cell so as to contact a surface of said reference electrode; and
a motor including means for rotating said shaft so that said surface of said indicator electrode is polished with said surface of said membrane and the surface of said reference electrode is polished with said buffer.

18. An electrode system for measuring oxygen gas in a solution, comprising:
a pair of electrodes including an indicator electrode and a reference electrode;
an oxygen permeable membrane covering said indicator electrode so as to separate said pair of electrodes from said solution to be analyzed;
an electrolytic cell mounting therein said pair of electrodes, filled with an electrolyte solution;
means for pressing a surface of said membrane against a surface of said indicator electrode, the contacting surfaces of said membrane and said indicator electrode being parallel; and
means for moving at least one of said indicator electrode and said membrane reciprocally in a direction parallel to said contacting surfaces so that the surface of said indicator electrode is rubbed with the surface of said membrane, thereby to be cleaned.

19. An electrode system for measuring oxygen gas in a solution, comprising:
a pair of electrodes including an indicator electrode and a reference electrode;
an oxygen permeable membrane covering said indicator electrode;
a shaft mounting said indicator electrode on an end surface thereof and said reference electrode surrounding said shaft on the side surface thereof;
an electrolytic cell having a bottom opening, mounting said shaft with a portion of said shaft extending out of said bottom opening, said cell being filled with an electrolyte solution;
means for pressing a surface of said membrane against a surface of said indicator electrode;
a body having a test chamber therein covering said membrane, said body having a channel opening into said chamber through which said solution to be analyzed flows;
a magnetic stirrer placed in said chamber;
a motor including means for rotating said shaft so that said surface of said indicator electrode is polished with said surface of said membrane; and
a magnet attached to an axle of said motor for rotating said magnetic stirrer.

20. An electrode system according to claim 19, further comprising means, including a buffer disposed in the wall of said electrolytic cell, for contacting and polishing a surface of said reference electrode.

21. An electrode system according to claim 18, wherein said magnetic stirrer contacts the surface of said membrane opposite said indicator electrode so as to rub said surface opposite said indicator electrode when said magnet rotates said magnetic stirrer.

* * * * *